(12) United States Patent
Striepe et al.

(10) Patent No.: US 8,543,197 B2
(45) Date of Patent: Sep. 24, 2013

(54) PORTABLE DEVICE AND METHOD FOR MEASURING HEART RATE

(75) Inventors: Harald Striepe, Boulder Creek, CA (US); Alfredo Knecht, Campbell, CA (US); Doc L. Childre, Boulder Creek, CA (US)

(73) Assignee: Quantum Intech, Inc., Boulder Creek, CA (US)

( * ) Notice: Subject to any disclaimer, the term of this patent is extended or adjusted under 35 U.S.C. 154(b) by 1330 days.

(21) Appl. No.: 11/818,142

(22) Filed: Jun. 12, 2007

(65) Prior Publication Data
US 2007/0299354 A1  Dec. 27, 2007

Related U.S. Application Data

(63) Continuation-in-part of application No. 11/528,955, filed on Sep. 27, 2006, now Pat. No. 7,462,151, which is a continuation of application No. 10/486,775, filed as application No. PCT/US00/05224 on Mar. 1, 2000, now Pat. No. 7,163,512, which is a continuation of application No. 09/260,643, filed on Mar. 2, 1999, now Pat. No. 6,358,201.

(60) Provisional application No. 60/813,151, filed on Jun. 12, 2006.

(51) Int. Cl.
*A61B 5/0205* (2006.01)

(52) U.S. Cl.
USPC .............................. 600/513; 600/508; 600/509

(58) Field of Classification Search
USPC .................. 600/508–509, 513, 516–517, 523
See application file for complete search history.

(56) References Cited

U.S. PATENT DOCUMENTS

| | | | | |
|---|---|---|---|---|
| 5,317,269 | A * | 5/1994 | Mills et al. | 324/427 |
| 5,755,671 | A * | 5/1998 | Albrecht et al. | 600/516 |
| 7,462,151 | B2 * | 12/2008 | Childre et al. | 600/300 |
| 2005/0113707 | A1 * | 5/2005 | Stabler et al. | 600/523 |

* cited by examiner

*Primary Examiner* — Joseph Stoklosa
(74) *Attorney, Agent, or Firm* — K&L Gates LLP

(57) ABSTRACT

A portable electronic device monitors the pulse or electrocardiogram of a person by integrated, attachable or wireless sensors. The portable device evaluates this data in real-time to assess heart rate variability coherence, and provide feedback through a variety of sounds and an array of LEDs. The feedback may be in the form of a breathing indicator or pacer usable as a respiratory cycle training system to indicate to the subject when the next breath should be taken. Such feedback may be correlated to the level of coherency the subject achieves. A coherence indicator may be used to provide the subject with real-time information relating to the level of coherence achieved.

30 Claims, 8 Drawing Sheets

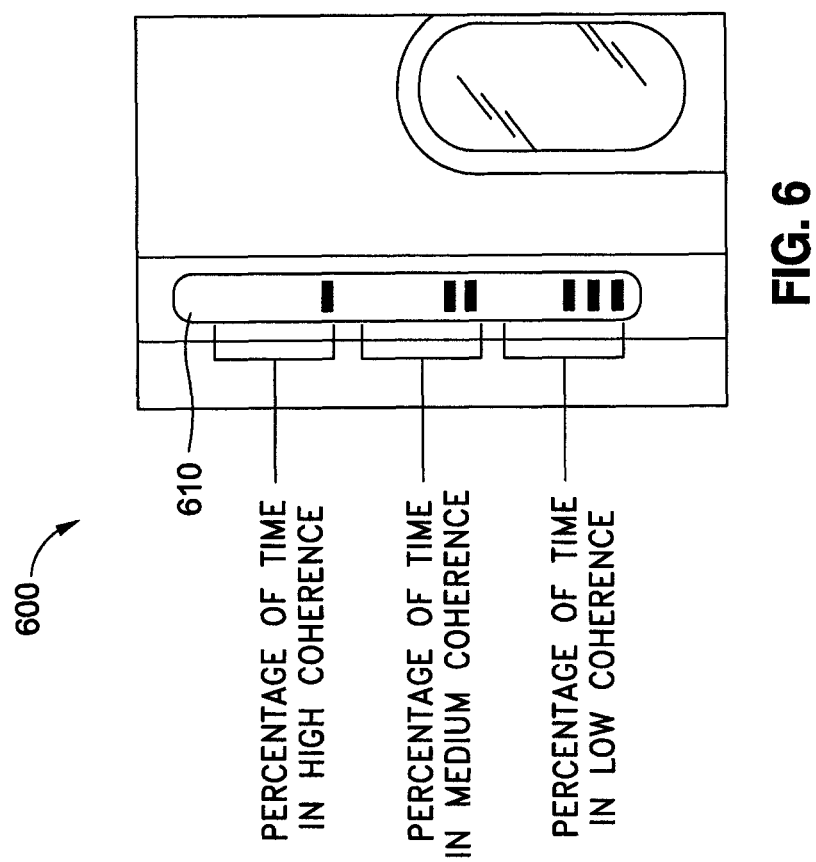

US 8,543,197 B2

PORTABLE DEVICE AND METHOD FOR MEASURING HEART RATE

CROSS-REFERENCE TO RELATED APPLICATIONS

This application is a continuation-in-part of application Ser. No. 11/528,955, which is a continuation of application Ser. No. 10/486,775, which is the National Stage of International Application No. PCT/US00/05224, filed Mar. 1, 2000, which is a continuation of U.S. application Ser. No. 09/260,643, filed Mar. 2, 1999, now U.S. Pat. No. 6,358,201. This application also claims the benefit of U.S. Provisional Application No. 60/813,151, filed Jun. 12, 2006.

FIELD OF THE INVENTION

The present invention relates generally to the evaluation of heart rate variability, and specifically to the analysis of the power spectrum distribution of the heart rate variability to assess physiological coherence and autonomic balance.

BACKGROUND OF THE INVENTION

Many studies have shown that stress and other emotional factors increase the risk of disease, reduce performance and productivity and severely restrict the quality of life. To this end, the medical communities around the world continually seek remedies and preventive plans. Recently, a focus on the self-regulation of systems within the body has led to research in the areas of increasing performance and facilitating recovery from numerous health challenges. Such research has suggested a causal link to, for example, enhanced academic performance, communication and listening skills, faster reaction times and better coordination.

In the last 25 years, a variety of new techniques have been introduced as alternatives to more traditional psychotherapies or pharmaceutical interventions for improving mental and/or emotional imbalances, reducing stress and improving performance. Devices have been designed for this purpose, some portable and some not. Portable devices capable of measuring heart rate are known for use in monitoring physical fitness activities. These devices tend to use heart rate sensors based on electrocardiogram (ECG) detectors, and are either embedded in a chest strap or use finger contacts on a watch. Other portable devices record a higher resolution ECG for the purpose of medical assessment or diagnosis (e.g., Halter Recorders). Thus, the two most commonly-used portable devices for heart-rate related measurements fall into two general categories: devices which track the average heart rate for physical fitness (HR monitors), and devices recording the ECG for the purposes of medical assessment, diagnosis or research.

The first category, which tends to use a wireless chest strap with an embedded ECG pickup, detects and averages the heart beat while displaying it on a watch or stopwatch like module. The second category are so-called Halter Recorders, and tend to use electrodes taped to the skin and tape or solid state media to record a full electrocardiogram over a period of time for later medical analysis. That is, there tends to be little feedback during the recording session. However, neither category of device is designed to improve physiological coherence or autonomic balance.

SUMMARY OF THE INVENTION

Disclosed and claimed herein is a portable device and method for improving the physiological coherence of a subject. In one embodiment, a portable electronic device includes a pulse sensor configured to receive pulse data from the subject, and a processor configured to determine a heart rate variability waveform based on the pulse data having a power spectrum distribution (PSD), and to determine a coherence level for the subject derived from a PSD peak of said pulse data PSD. The portable electronic device further includes a coherence indicator, electrically connected to the processor, and configured to provide a coherence indication representative of the coherence level of the subject, as well as a respiration indicator configured to prompt the subject to breath at a desired respiration frequency which is associated with an increased coherence level.

Other aspects, features, and techniques of the invention will be apparent to one skilled in the relevant art in view of the following description of the exemplary embodiments of the invention.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein:

FIGS. 5-7 illustrate various embodiments of how coherence information may be provided to a subject user.

DETAILED DESCRIPTION OF THE PREFERRED EMBODIMENTS

I. Background

Figure 1A:
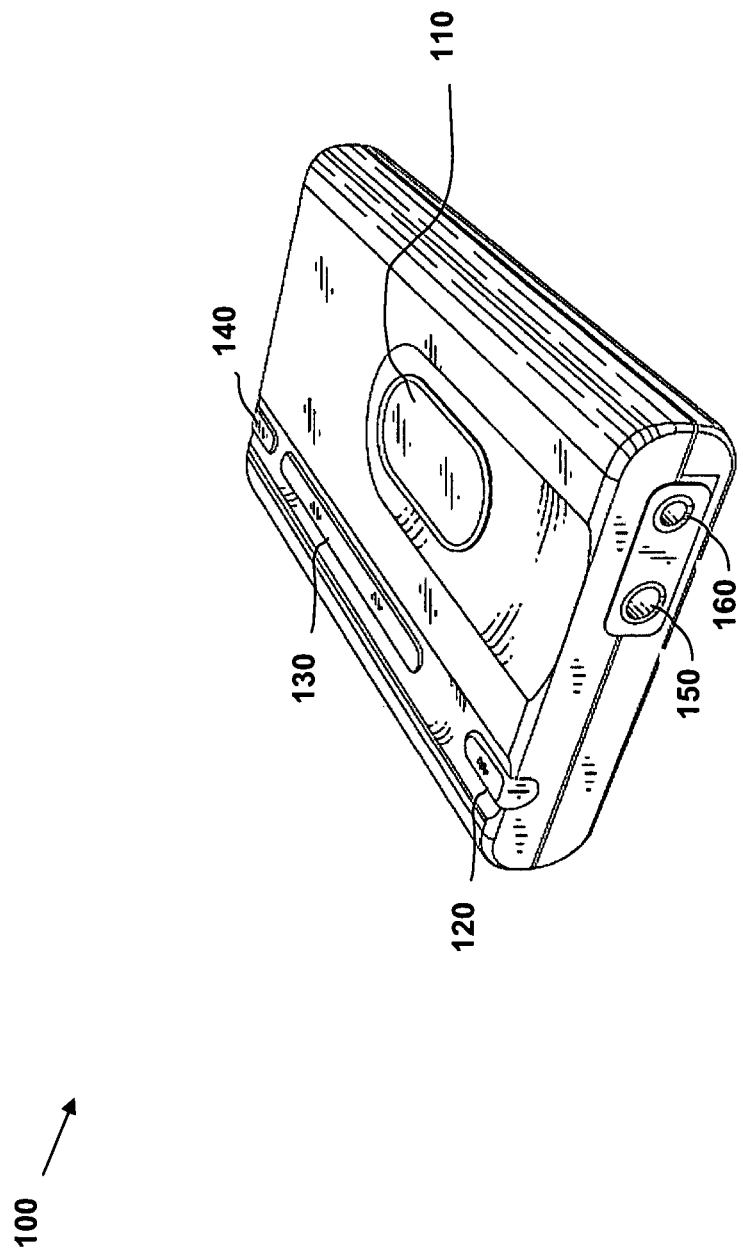
FIG. 1A depicts one embodiment of a portable device for implementing one or more aspects of the invention.

As disclosed in the parent application hereto, U.S. Pat. No. 6,358,201 (the '201 patent), Freeze-Frame® is one tool that may be used for mental and emotional self-management and performance enhancement. It consists of consciously disengaging the mental and emotional reactions to either external or internal events and then shifting one's center of attention to the physical area around the heart and breathing as if you are breathing through the heart at a rhythm of 5 seconds on the in-breath and 5 seconds on the out-breath as if you are breathing out through the solar plexus. These steps facilitate a shift in the heart's rhythmic beating pattern. The next step is to intentionally shift one's emotional state by focusing on a positive emotion such as love, care or appreciation. In one embodiment, this emotional shift stabilizes the coherent physiological mode and takes the process past what can be achieved with breathing techniques alone. This tool thus allows the individual to shift focus of attention from the mind to the heart. Such a shift results in a wider and more objective perception in the moment.

We use the term "coherence" in a broad context to describe more ordered mental and emotional processes as well as more ordered and harmonious interactions among various physiological systems. In this context, "coherence" embraces many other terms that are used to describe specific functional modes, such as synchronization, entrainment, and resonance.

Physiological coherence is characterized by both autocoherence and cross-coherence in the activity of physiological systems. For example, this mode is associated with increased coherence in breathing rhythms and the heart's rhythmic activity, which manifests as a sine wave-like heart rhythm pattern (autocoherence). Additionally, during this mode there also tends to be increased cross-coherence or entrainment among different physiological oscillatory systems, including the heart rhythms, respiratory rhythms, and blood pressure waves.

A related phenomenon that occurs during physiological coherence is resonance. In physics, resonance refers to a phenomenon whereby an unusually large vibration is produced in a system in response to a stimulus whose frequency is the same as, or nearly the same as, the natural vibratory frequency of the system. The frequency of the vibration produced in such a state is said to be the resonant frequency of the system. When the human system is operating in the coherent mode, increased synchronization occurs between the sympathetic and parasympathetic branches of the ANS, and entrainment occurs among the heart rhythms, respiratory rhythms, and blood pressure oscillations and can also occur among very low-frequency brain rhythms, craniosacral rhythms, and electrical potentials measured almost anywhere across the skin. This occurs because these oscillatory subsystems are all vibrating at the resonant frequency of the system.

In terms of physiological functioning, physiological coherence or resonance confers a number of benefits to the system. For example, there is increased cardiac output in conjunction with increased efficiency in fluid exchange, filtration, and absorption between the capillaries and tissues; increased ability of the cardiovascular system to adapt to circulatory requirements; and increased temporal synchronization of cells throughout the body. This results in increased system-wide energy efficiency and metabolic energy savings. These findings provide a link between positive emotions and increased physiological efficiency, which may partly explain the growing number of correlations documented between positive emotions, improved health, and increased longevity.

It is possible to have entrainment between the heart rhythm and respiration without entrainment with other physiological systems. This can occur in the high frequency range of the HRV power spectrum, which is associated with respiratory sinus arrhythmia (RSA). Although this type of entrainment represents a more ordered form of RSA, it is not reflective of the more system-wide coherence or resonance that we are describing here. Respiratory sinus arrhythmia biofeedback training has focused on increasing the amount of HRV in the high frequency region of the power spectrum. The process described here is fundamentally different as it facilitates the coherent or resonant physiological mode.

The respiratory rhythm can be utilized to facilitate coherence because it modulates the heart rhythm. This is why taking a few deep breaths during a stressful time can be helpful because breathing patterns modulate heart rhythms and heart rhythms have powerful body-wide effects, including a change in the afferent neural patterns sent to the brain from the heart. However, for the coherent mode to emerge, the breathing rate should be at the correct frequency.

The nervous system mechanisms coupling breathing and heart rhythms are complex and there is no universal understanding as to the mechanisms underlying the generation of RSA. Autonomic response systems are continuously being updated and regulated via complex feedback systems. These feedback loops, typical of many regulatory processes, produce a rhythmic pattern characterized by phasic increases and decrease in neural efferent and afferent activity between organs such as the lungs, heart and brain. Often, as in the case of heart rate, there are numerous feedback influences and, thus, the response is composed of the sum of numerous rhythmic components. Within normal parameters, greater amplitude of oscillation is associated with health. Thus, the amplitude of rhythmic physiological processes may index the status of the individual's nervous system and capacity to respond. In other words, the greater the amplitude of "organized" rhythmic physiological variability, the greater the response potential or possible range of behavior.

The three primary mechanisms generally proposed to explain the modulation of heart rate associated with respiration are: (1) a direct influence of medullary respiratory neurons on cardiomotor neurons; (2) an indirect influence on heart rate of blood pressure changes secondary to respiratory movements that is mediated via arterial baroreceptors or atrial stretch receptors; and (3) a reflex response to lung inflation mediated by thoracic stretch receptors, most likely from the lungs and chest wall.

Although both supportive and contrary evidence exists for most of the mechanisms listed above, it is likely that each of them plays at least some role in generating RSA. Thus, RSA reflects the complex effects of central respiratory drive on the integration of autonomic afferent signals and the production of autonomic efferent signals in the brain stem, and of respiratory mechanics on the cardiovascular structures within the thorax. The phenomenon is dependent on the frequency and amplitude of respiration, as well as on the underlying autonomic state of the organism. The magnitude and phase characteristics of RSA during different physiological states suggest that it is mediated by respiratory modulation of both cardiac sympathetic and vagal efferent activity, and mechanical stretch of the lungs.

The fact that respiration modulates the heart rhythm makes it a powerful intervention that can have quick and profound body-wide effects, if it is used to drive the coherent mode and this requires knowing the appropriate breathing rate.

We have found that as the respiratory rate is lowered, there is a point at which the heart rate variability pattern, blood pressure rhythm and respiratory rhythms suddenly entrain. In essence, the system shifts modes and operates at its resonance frequency. As described in the '201 patent, which is hereby fully incorporated by reference, this frequency is around 0.1 Hz for most people. However, there is a range of frequencies between 0.03125 Hertz and 0.234 Hertz in which the coherent mode can be observed in the majority of people. In terms of respiration, this would mean we would expect the rhythm to vary about one breath per minute around each side of the resonant frequency which is typically a ten second rhythm (0.1 Hertz).

As used herein, physiological coherence is characterized by a narrow band high amplitude signal in the LF region of the HRV power spectrum, with no other significant peaks in the very low frequency (VLF) or high frequency (HF) region, and a relatively harmonic signal (sine-wave-like), in the time domain trace of the HRV data.

As used herein, the terms "a" or "an" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Reference throughout this document to "one embodiment", "certain embodiments", "an embodiment" or similar term means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner on one or more embodiments without limitation.

In accordance with the practices of persons skilled in the art of computer programming, the invention is described below with reference to operations that are performed by a computer system or a like electronic system. Such operations are sometimes referred to as being computer-executed. It will be appreciated that operations that are symbolically represented include the manipulation by a processor, such as a central processing unit, of electrical signals representing data bits and the maintenance of data bits at memory locations, such as in system memory, as well as other processing of signals. The memory locations where data bits are maintained are physical locations that have particular electrical, magnetic, optical, or organic properties corresponding to the data bits.

When implemented in software, the elements of the invention are essentially the code segments to perform the necessary tasks. The code segments can be stored in a processor readable medium or transmitted by a computer data signal. The "processor readable medium" may include any medium that can store or transfer information. Examples of the processor readable medium include an electronic circuit, a semiconductor memory device, a ROM, a flash memory or other non-volatile memory, a floppy diskette, a CD-ROM, an optical disk, a hard disk, a fiber optic medium, a radio frequency (RF) link, etc.

II. Coherence Training & Feedback

As will be described in more detail below, an optimal number of breaths per minute is known or determined. In one embodiment, this optimal number may be based in part on the peak-to-peak interval for the coherence peak in the HRV power spectrum. The optimal number of breaths may be considered the point at which the HRV pattern, blood pressure rhythm and respiratory rhythm entrain (referred to herein as the resonant frequency). While this frequency may be approximately 0.1 Hz, in another embodiment, the resonant frequency may be in the range of between 0.03125 Hertz and 0.234 Hertz.

As will be described in more detail below, a subject's coherence level may be determined in accordance with the principles disclosed in the '201 patent. Once that information is determined, the breathing indicator or pacer may be used as a respiratory cycle training system to indicate to the subject when the next breath should be taken.

Another aspect of the invention is to provide guidance and feedback that is correlated to the level of coherency the subject achieves. As will be described in more detail below, a coherence indicator may be used to provide the subject with real-time information relating to the level of coherence achieved.

Referring now to the figures, FIG. 1A depicts one embodiment of a portable device configured in accordance with the principles of the invention. As shown, device 100 includes a physiological sensor 110, which in one embodiment may be an optical pulse monitor (plethysmograph), an electrocardiogram (ECG) sensor or the like. While in one embodiment sensor 110 may be integrated with an operating switch of the device 100, in another embodiment the sensor 110 may be clipped to a subject's ear lobe, for example. Similarly, the sensor 110 may be in the form of a chest strap or any other physiological sensor configuration. As such, it should be appreciated that numerous other sensor configurations are possible and within the scope of the present disclosure. In another embodiment, the sensor 110 may also act as an operating button which can be activated by tilting the sensor 110 through a central pivot and depressing either the top or bottom of the area occupied by the sensor 110. In this fashion, the sensor 110 may perform both physiological sensing (e.g., pulse, ECG, etc.) and device operating functions. In certain embodiments, the sensor 110 may perform different functions depending on the length of time it is depressed by the subject. For example, the sensor 110 may function to receive pulse data when contacted by a subject, but not depressed. Thereafter, a first function (e.g., change challenge level, brightness, volume, etc.) may be associated with a short depression, a second function (e.g., change display options for heart rhythm pattern or HVR data) associated with a long depression, while a third function (e.g., on/off) may be associated with a very long or 'hold' depression. It should be appreciated that the specific operational functions, and triggering thereof, of the sensor 110 may vary.

Device 100 is further equipped with one or more visual indicators. In particular, a pulse indicator 120 may be included for providing feedback to the user representative of the user's current pulse rate. While indicator 120 is referred to herein as being a pulse indicator, it should equally be appreciated that it may be configured to provide information corresponding to some other physiological characteristic, such as when the sensor 110 is a physiological sensor other than a pulse sensor (e.g., ECG sensor). Therefore, each reference to the pulse indicator 120 should be understood to include reference to an indicator of any other physiological characteristic.

The pulse indicator 120 may comprise one or more light emitting diodes (LED) which blink (or otherwise illuminate) each time a pulse is detected. The pulse indicator 120 may further comprise one or more multi-colored LEDs, and may further incorporate the use of audio tones. A user's pulse may be read by either placing the thumb lightly on the sensor 110, or by use of an ear sensor clipped to the user's ear lobe, as mentioned above. In certain embodiments, the device may accumulate pulse data from the sensor 110 in order to determine the user's Heart Rate Variability (HRV). As will be described in more detail below, the HRV data may then be used to determine an overall coherency value for the user.

Another aspect of the invention is to provide a breath pacer which prompts or otherwise trains the user to take breaths at particular intervals. To that end, action indicator 130 is provided and includes a series of LEDs. In one embodiment, the LEDs of action indicator 130 illuminate in a rising and falling sequence so as to emulate the inhaling and exhaling portions of breathing. By way of example, the action indicator 130 may illuminate the LEDs in a tear-drop-like movement pattern with trailing lights so as to impart the visual effect that the light is actually moving along the action indicator 130. To that end, FIG. 1B depicts one embodiment of the action indicator 130 showing an "breath in" indication, while FIG. 1C depicts one embodiment of the action indicator 130 during a "breath out" indication. In addition to providing an animated LED sequence, the action indicator 130 may similarly use multiple levels of apparent brightness, and/or use multiple dynamic elements overlaid. In another embodiment, the action indicator 130 may comprise other display devices, such as color LCD, organic LED (OLED), etc.

Referring back to FIG. 1A, device 100 is further shown as including a coherence indicator 140. In one embodiment, the coherence indicator 140 provides a visual feedback of the user's current coherency level, based on the current challenge level. That is, a low coherency state may be associated with the coherence indicator 140 illuminating in red light, while a medium state of coherency may result in the coherence indicator 140 illuminating as blue. Similarly, a high coherency state may result in the coherence indicator 140 illuminating as green. It should of course be appreciated that the level of coherence indicated by the indicator 140 may be reflected in other colors, as a series of illuminations, as sounds, or as any other known feedback means. The device 100 may further include an AC adapter jack 150 for powering the device from an external AC power source. In another embodiment the device 100 may be battery powered, or powered through any other known means. Sensor jack 160 may used to receive an ear loop sensor adapter, as mentioned above.

As previously mentioned, the device 100 may be powered on by pressing sensor 110 (either top portion or bottom portion) for a predetermined period of time (e.g., 1-2 seconds). The device 100 may then cycle through a self-test and display a characteristic animation of certain LEDs, including for example color cycling of the coherence indicator 140 and/or pulse indicator 120. This process may be accompanied by a characteristic sound effect. In certain embodiments, the device 100 may include a power-off feature such that it will power off if no pulse is detected for some period of time (e.g., 1 minute).

Another aspect of the invention is to provide varying levels of difficulty in achieving a desired state (e.g., coherency). To that end, in one embodiment the device 100 may be placed in any one of 4 discrete "challenge levels," which increase the coherence threshold that must achieved to change the coherence indicator 140 (e.g. from red to blue, from red to green, etc.). During a setup mode, for example, the user may select the challenge level by pressing, for example, sensor 110, or a portion thereof (i.e., top portion or bottom portion). In another embodiment, the user may also be given the option of setting the brightness level for the various LEDs of the device 100, as well as the volume level for any audio outputs.

Figure 1D:
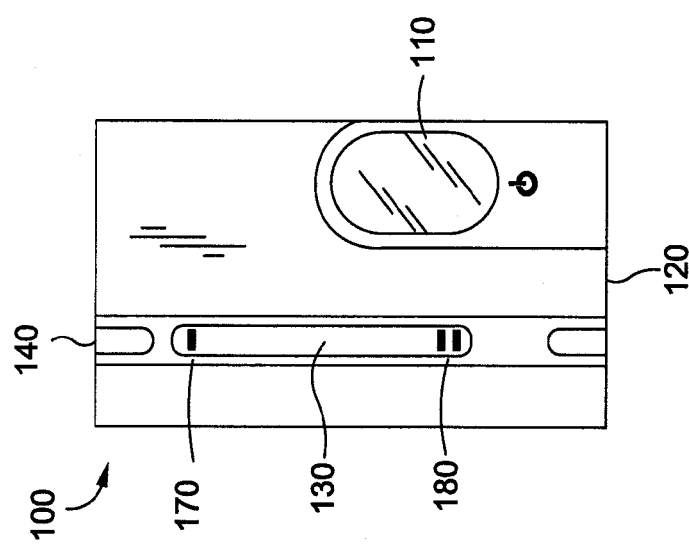
FIG. 1D depicts additional aspects of the portable device of FIG. 1A.
Figure 1C:
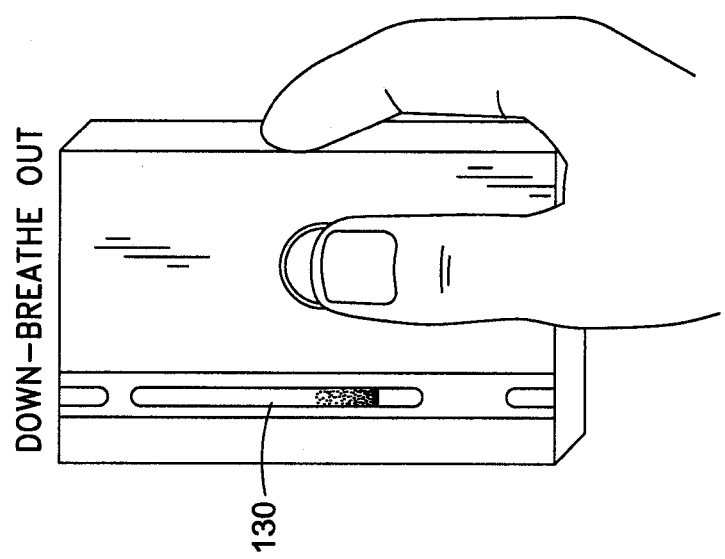
FIGS. 1B-1C depict a breathing indicator in accordance with one embodiment.
Figure 1B:
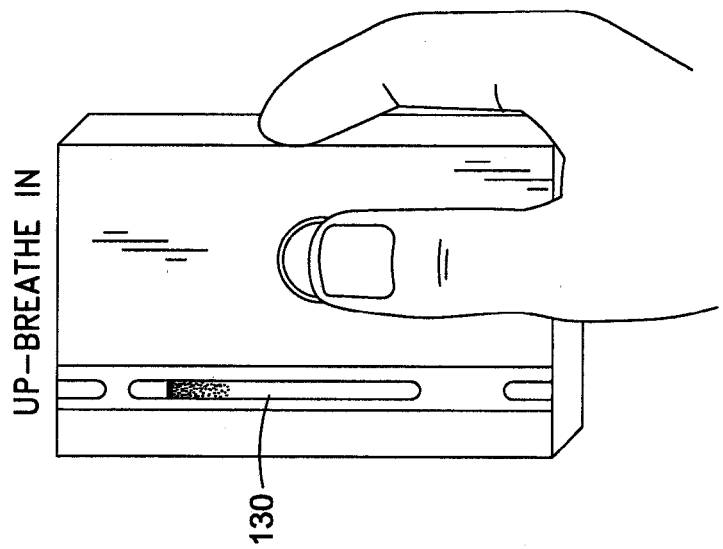
Figure 2:
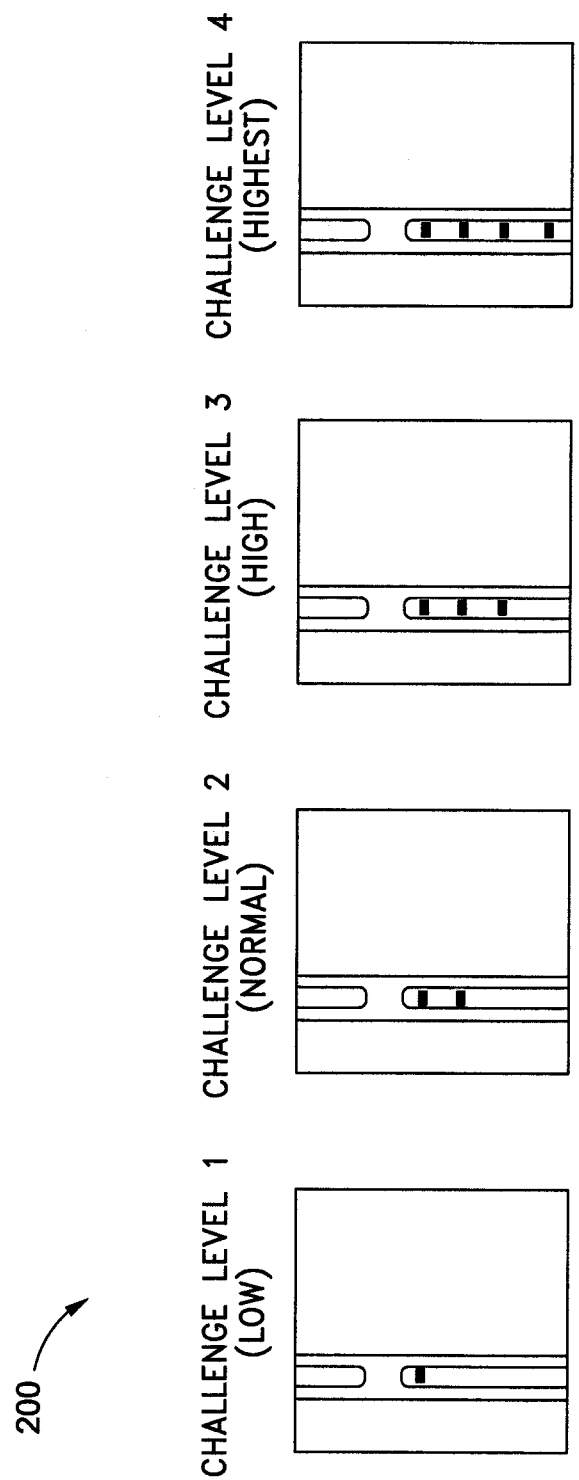
FIG. 2 depicts available coherence challenge levels for one embodiment of the portable device of FIG. 1A.

With reference to FIG. 1D, the action indicator 130 may be used to simultaneously display both the coherence challenge level 170 (i.e., level 1), as well as the current brightness setting 180 (i.e., setting 2). By successively pressing the sensor 110 the currently-selected challenge level may be incremented. To denote the currently-selected challenge level, a number of LEDs equal to the challenge level may be illuminated, as shown in sequence 200 of FIG. 2, wherein one LED represents challenge level 1, two LEDs represent challenge level 2, and so on.

As described with reference to FIGS. 1A-1D, the sensor 110 may perform both pulse sensing and device operating functions. That is, in addition to being configured to receive pulse data from a subject (e.g., upon the subject's finger contacting the sensor 110), the sensor may further be configured to perform various operational functions depending on the length of time the sensor 110 it is depressed by the subject, and/or the portion of the sensor which is depressed (e.g., top or bottom portion).

Figure 3:
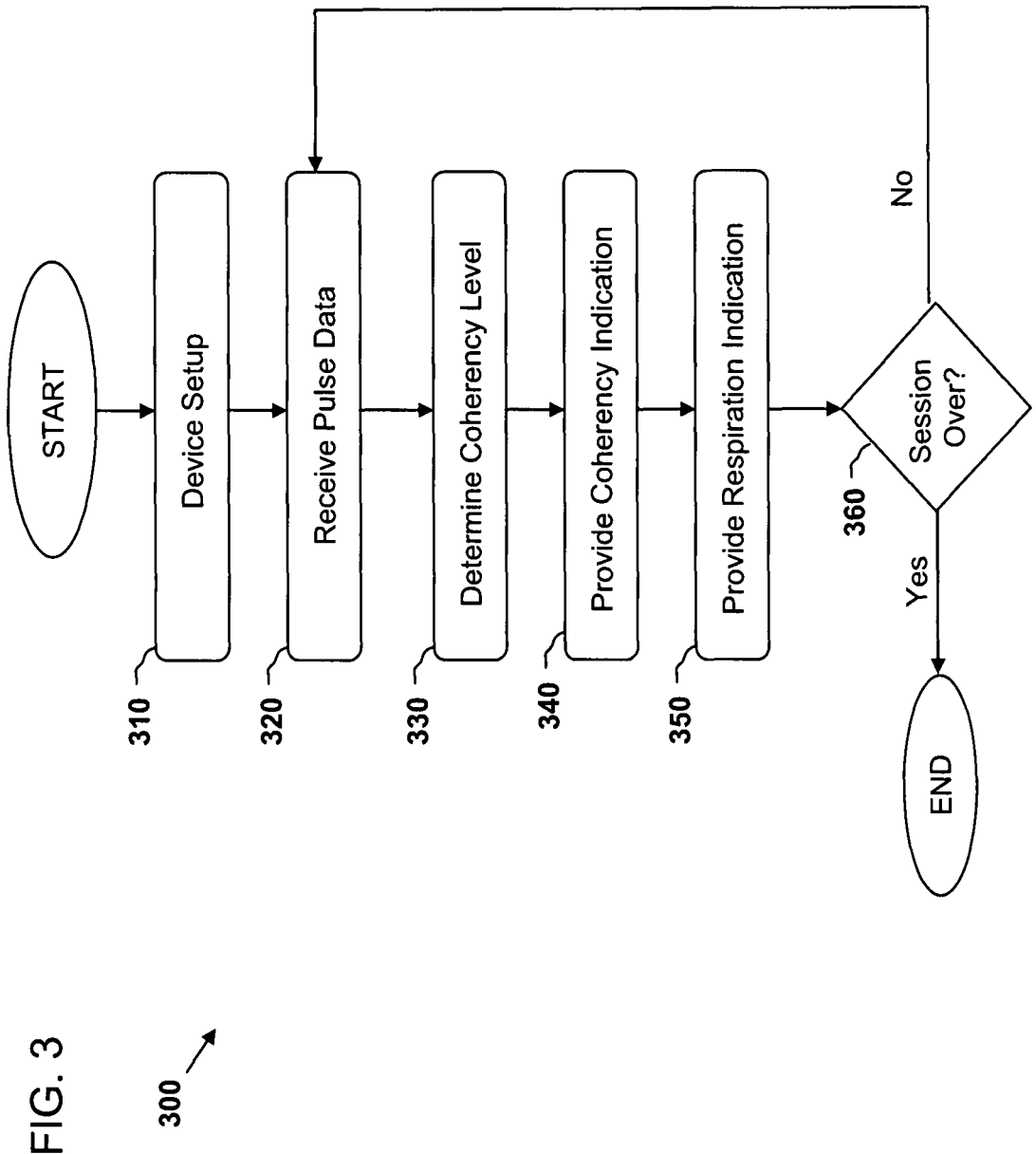
FIG. 3 illustrates one embodiment of a process for implementing certain aspects of the invention.

FIG. 3 depicts an embodiment of a process 300 for carrying out one or more aspects of the invention. In particular, process 300 begins at block 310 with the optional setup of a portable device (e.g., device 100) configured to carry out one or more aspects of the invention. In one embodiment, the device setup (which may be preformed at power on) may include the previously-described challenge level and brightness adjustments. In other embodiments, the operation of block 310 may include the setup of other parameters as well, or instead.

Once the device is setup, process 300 may continue to block 320 where the subject's pulse data may be received. In one embodiment, such pulse data may be detected by sensor 110 of FIG. 1A, which may be in the form of a sensor button, ear sensor, or any other sensor capable of detecting pulse data. In certain embodiments, the operation of block 320 may include a calibration phase during which pulse data is collected and used to calibrate the sensitivity of the sensor for optimal pulse detection. Whether or not the sensor is calibrated, pulse data is collected at block 320 for the current active training session.

Continuing to refer to FIG. 3, process 300 may then continue to block 330 where the pulse data received at block 320 may be used to determine a coherency state for the subject. In one embodiment, the method used to determine and represent the subject's coherency state may be as disclosed in the parent '201 patent. However, it should equally be appreciated that other method and algorithms may similarly be used in accordance with the principles of the present invention.

In one embodiment, the coherence level may be based on an entrainment parameter (EP), as described in detail in the parent '201 patent. Based on the pulse data of block 320, HRV data is obtained and processed to produce an EP score. This EP score may represent a measure of the strength. (or relative height) of the highest peak (i.e., coherence peak) within a selected range of the power spectrum distribution (PSD) of the HRV waveform. The instantaneous EP score may then be used to determine a level of coherence—low, medium or high, which may also be a function of the selected challenge level. In general, maximum coherence may be reached when the coherence peak contains a large portion of the total power within the PSD of the HRV waveform.

In another embodiment, the relative amplitude of the coherence peak may be used directed as a measure of the subject's level of coherence. While this frequency may be approximately 0.1 Hz, in another embodiment, this resonant frequency may be in the range of between 0.03125 Hertz and 0.234 Hertz. Additionally, it should be appreciated that the coherence peak tends to shift within this coherence range between subjects, and even over time for the same subject. As such, the operation of block 330 may be recursive in nature. The discovery that a subject's state of coherency is a dynamically changing state, requires that the coherency peak be dynamically tracked in order to accurately detect the subject's coherence state. It should further be appreciated that such coherency level may be determined and/or represented in either of the time domain or frequency domain.

Continuing to refer to FIG. 3, once the subject's instantaneous coherence level is determined, process 300 may then continue to block 340 where a coherence indication may be provided to the subject. In one embodiment, the coherence indication may be provided by the coherence indicator 140 of FIG. 1A, for example.

A determination at block 330 that the subject is in a state of low coherence may be associated with the coherence indicator illuminating a red LED at block 340. Once the subject achieves a medium coherence level (e.g., based on the chosen challenge level), the coherence indication of block 340 may instead be the illumination of a blue LED. Similarly, a high coherence level may be associated with a coherence indication at block 340 comprising of a green LED. It should of course be appreciated that any other number of colors, or variations of colors may be used at block 340, and that such coherence indication may take other forms (e.g., audio indication).

Process 300 continues to block 350 where a respiration indication may then be provided to the subject. In one embodiment, the respiration indication may be provided using the action indicator 130 described above with reference to FIG. 1A. The respiration indication of block 350 may comprise illuminating a rising and falling sequence of LEDs so as to simulate the inhaling and exhaling portions of breathing. By way of example, a series of LEDs in a tear-drop-like movement pattern with trailing lights may be displayed so as to impart the visual effect that the light is actually moving, such as the sequence depicted in FIGS. 1B-1C.

Regardless of the form of the indication provided at block 340, in one embodiment the respiration indication is used to aid the subject in knowing when to breath so as to achieve an optimal breathing frequency. While the optimal breathing frequency may vary from subject to subject, in one embodiment it is approximately six (6) breaths per minute. As will be described below with reference to FIG. 4, the respiration indication may be tailored to the specific subject by adjusting the frequency of the respiration indication provided at block 350.

At this point, process 300 will return to block 320 where additional pulse data may be collected. In this fashion, the process 300 is intended to encourage the subject to move towards a higher coherency state through the respiration training function of block 350, while simultaneously providing the user with feedback representative of the achieved level of coherency.

Figure 4:
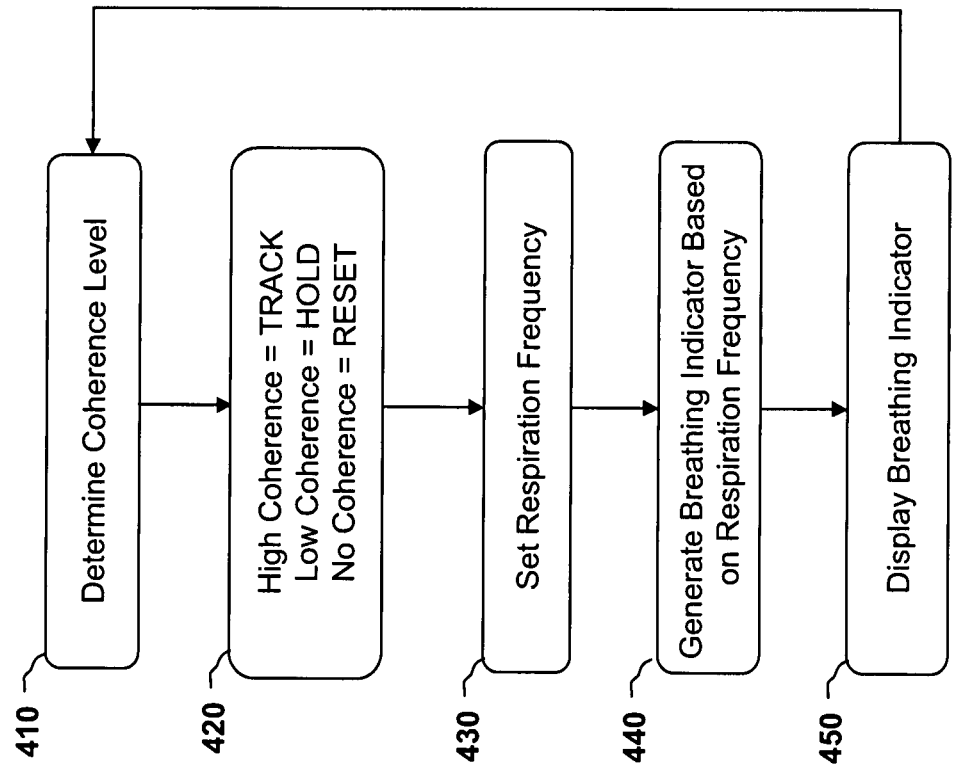
FIG. 4 illustrates another embodiment of a process for implementing certain aspects of the invention.

Referring now to FIG. 4, depicted is one embodiment of a process 400 for how the respiration indication of block 350 may be adjusting to take into account the natural variation in the resonant frequency from one subject to the next. Specifically, process 400 begins at block 410 where the coherence level of the subject is determined. In one embodiment, this operation may be the operation described and performed above at block 330 of FIG. 3. Once the coherence level is determined (either at block 410 of FIG. 4 or block 350 of FIG. 3), process 400 may continue to block 420 where a breath pacing scheme may be selected based on the current coherence level. In particular, a respiration frequency may be tracked, held or reset based on the computed coherence level.

In certain embodiments, the respiration frequency is gradually adjusted between the three values termed TRACK, HOLD and RESET (block 420), 'TRACK' identifies the detected peak frequency in the frequency domain power spectrum. 'HOLD' identifies the most recently valid frequency, while RESET identifies a frequency characteristic of the user. Adjustment towards the TRACK frequency may occur in a state of medium or high coherence (determined at block 410, for example). If the state is instead a low coherence, the adjustment may gradually move towards the HOLD frequency, whereby the most recent actively-used respiration frequency will be held.

If, on the other hand, the system detects a very low coherence level, or if no measure of coherence level is available (e.g., at startup), the adjustment may gradually move towards the RESET position, when the RESET frequency will serve as the respiration frequency. The RESET frequency may be calculated by integrating the generated respiration frequency over some period of time. The RESET frequency may be stored (e.g., in nonvolatile memory), from where it can be recalled on subsequent startups.

Once the respiration frequency is correlated to the current coherence level at block 420, process 400 may continue to block 430 where the appropriate respiration frequency may be set. Again, the TRACK frequency will be set at block 420 for a high coherence (as well as medium coherence in some embodiments), where the TRACK frequency corresponds to the detected peak frequency in the power spectrum distribution of the collected HRV waveform data. A HOLD frequency may be set at block 430 for a low coherence state, where the HOLD frequency may be the last-used frequency, and so on.

Once the respiration frequency has been set, the breathing indicator may be generated at block 440, and then displayed at block 450. As previously mentioned, the breathing indicator may be in the form of a series of LEDs in a tear-drop-like movement pattern with trailing lights, one embodiment of which is depicted in FIGS. 1B-1C. In this fashion, the respiratory period detected through the pulse may be used to gradually adjust the breathing indicator towards the naturally emergent cycle of the subject.

In certain embodiments, the portable device of the invention may operate in one of two display modes during a training session—basic mode and advanced mode. In one embodiment, basic mode may include using the action indicator 130 to display a breathing indicator or pacer (e.g., indicator 130 shown in FIG. 1B-1C), followed by a short session summary display. In advanced mode, however, additional data may be presented to the subject using the action indicator 130.

Figure 5:
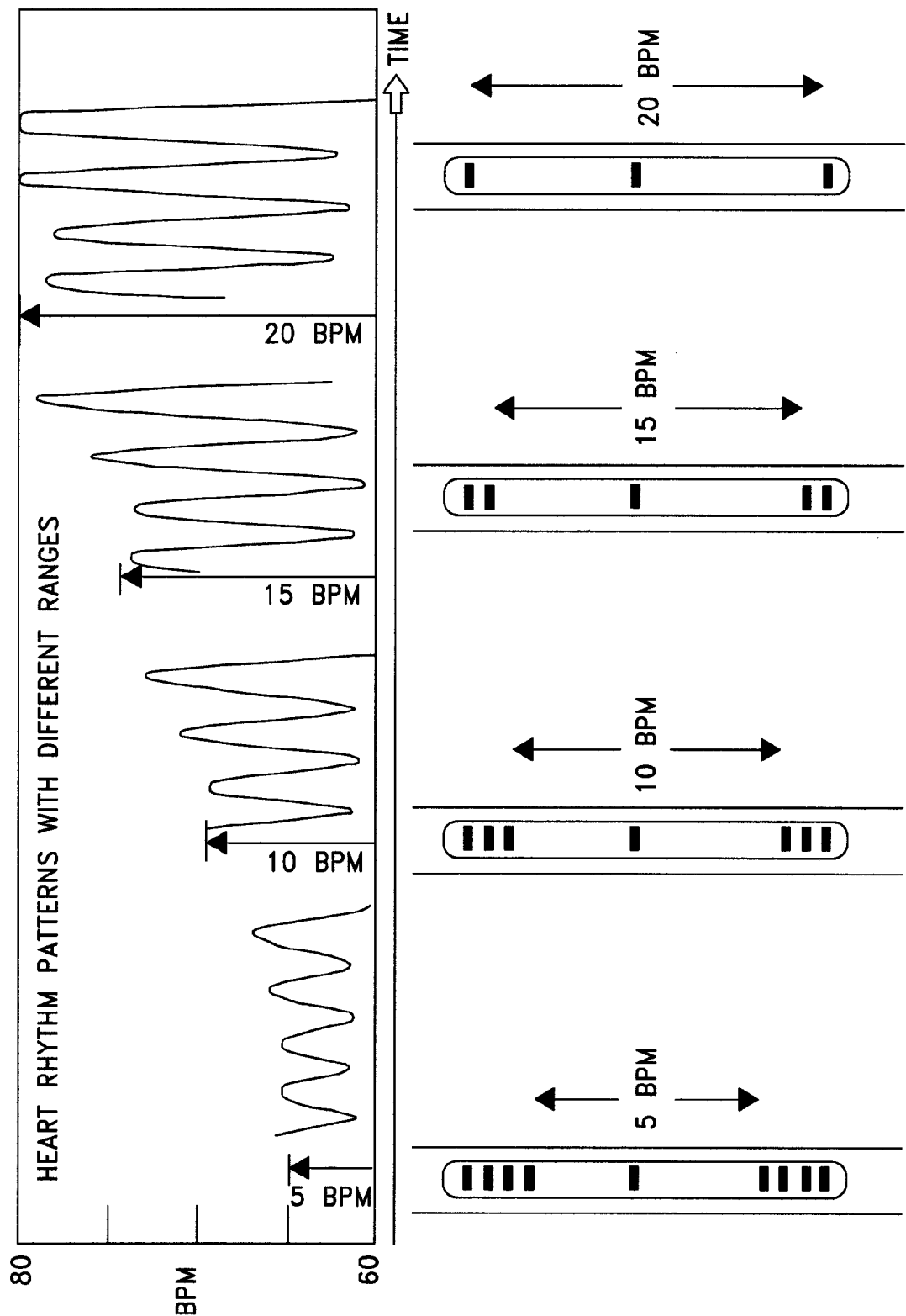

Additional information which may be presented using an action indicator of the portable device of the invention, such as action indicator 130, may include HRV data, such as the patterns depicted in FIG. 5 for example. As shown, the relatively small dynamic range of an action indicator (e.g., action indicator 130) may be mapped to the relatively large range of HRV data representing that of a typical subject. In other words, the action indicator represented by lit LEDs is mapped in comparison to a typical strip chart recorder. The effective magnification of the display may be switched across four ranges, with the range being displayed by brightly lit LEDs at the top and bottom of the display. The highest range/lowest "magnification" is represented by a single LED at the top and bottom, the lowest range/highest magnification is displayed by four lit LEDs, which also leave the smallest window. In this fashion, the action indicator may follow the HRV values indicating from relatively low to high from bottom to top.

In certain embodiments, the action indicator 130 may display HRV data in a fashion which assists the subject to increase his/her HRV range. Since lower HRV is associated with decreased fitness and is predictive of future health issues, providing visual feedback to a subject representative of their HRV data may serve to assist or train the subject to increase their HRV range. In addition, coherence training can have a positive impact on increasing both short and long-term HRV levels An additional example of information which may be presented using an action indicator of the portable device of the invention, such as action indicator 130, is depicted in FIG. 6. As shown, portable device 600 includes action indicator 610 configured to represent a session summary for a subject. In the embodiment of FIG. 6, the percentage of the session spent in any one coherence level may be shown by illuminating a number of LEDs representative of such percentage. For example, the indicator 610 of FIG. 6 shows that the subject spent 3 times as long in a low coherence state than in a high coherence state.

Figure 7C:
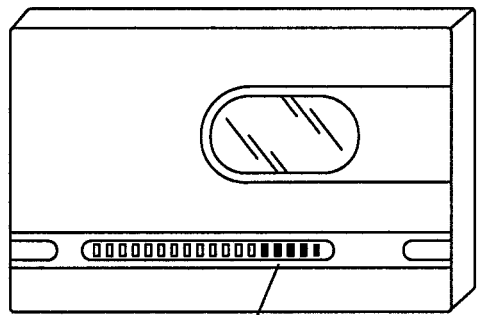
Figure 7B:
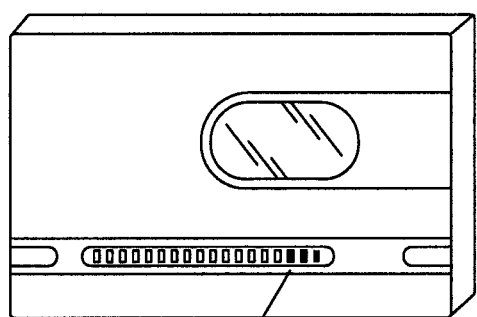
Figure 7A:
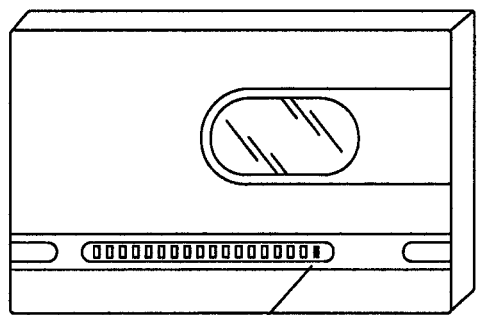

Referring now to FIGS. 7A-7C, another embodiment of how an action indicator of the invention may be used to provide more advanced information to a subject is depicted. Since a subject's performance over the duration of the session may be tracked, an accumulated coherence score may be derived therefrom. To that end, FIGS. 7A-7C illustrate how a cumulative coherence score may be maintained and displayed to a subject using an action indicator (e.g., action indicator 130). In certain embodiments, medium and high coherence may increment this cumulative score, while low coherence may decrement the score. As shown, the score may be indicated by a bar of LEDs.

Other embodiments may extend the sensor input (e.g., sensor 110 of FIG. 1A) by permitting wireless, remote sensing using a electrocardiogram (ECG) pickup embedded with a small radio transmitter in a chest strap or garment. In another embodiment, session data may be stored and/or reconciled with databases on a PC or server for remote viewing and analysis.

Additionally, the display capabilities described herein may be enhanced to allow interactions with games stored or downloaded to the portable device, which are controlled/manipulated according to the subject's coherence level.

Real-time session communication via any known wireless protocol may similarly be employed to transmit session data from the portable device to a remote device (e.g., PC, PDA, cellphone, etc.) for data storage or other interactive displays such as games.

Certain other functionality may be embedded in a wireless headset featuring an integrated pulse sensor. The invention may provide user feedback via audio, and communicate to other devices via any known wireless protocol or other forms of short distance radio for the purposes outlined herein.

A portable device configured in accordance with the principles of the invention may also function as an attachment to a musical playing device such as an MP3 player, using its display for user feedback, and controlling music playlists and other audio through the user's coherence.

Feedback may similarly be provided using low levels of vibration, such as a low frequency vibration for medium coherence, and higher frequency for high coherence, and so on. Similarly, one or more pulses of vibration may be used to indicate transitions from low to medium to high coherence.

References to pulse data, pulse sensors and pulse indicators are intended to represent specific embodiments of the invention, and not intended to limit the invention from including corresponding data, sensors and indicators for other physiological characteristics of the subject, such as ECG data, sensors and indicators.

While the invention has been described in connection with various embodiments, it should be understood that the invention is capable of further modifications. This application is intended to cover any variations, uses or adaptation of the invention following, in general, the principles of the invention, and including such departures from the present disclosure as come within the known and customary practice within the art to which the invention pertains.

The invention claimed is:

1. A portable electronic device comprising:
 a pulse sensor configured to receive pulse data from a subject;
 a processor electrically connected to the pulse sensor, wherein the processor is configured to determine a power spectrum distribution of the pulse data, to determine a heart rate variability waveform based on the pulse data having a power spectrum distribution (PSD), to determine a coherence level for the subject derived from a PSD peak of said PSD, and to track the PSD peak of the PSD, wherein the PSD peak has an amplitude and frequency which vary over time;
 a coherence indicator electrically connected to the processor and configured to provide a coherence indication representative of the coherence level of the subject; and
 a respiration indicator electrically connected to the processor and configured to prompt the subject to breath at a desired respiration frequency which is associated with an increased coherence level.

2. The portable electronic device of claim 1, wherein the respiration indicator comprises a plurality of light emitting diodes configured to illuminate in a moving pattern of trailing lights.

3. The portable electronic device of claim 1, wherein the coherence level is further based on a user-selectable coherence challenge level.

4. The portable electronic device of claim 1, wherein the processor is further configured to adjust the desired respiration frequency to account for the subject's natural respiration cycle.

5. The portable electronic device of claim 1, wherein the processor is configured to
 determine the coherence level as a function of a relative amplitude of the PSD peak to a plurality of other peaks in the PSD.

6. The portable electronic device of claim 5, wherein the coherence level increases as the PSD peak approaches the frequency range of between 0.03125 Hertz and 0.234 Hertz.

7. The portable electronic device of claim 1, wherein the coherence level is characterized by at least one of a state of relaxation and increased positive emotions.

8. The portable electronic device of claim 1, wherein the coherence level is characterized by a heart rate variability waveform having a sine-wave shape, and wherein the waveform is one of a respiratory sinus arrhythmia wave and a heart rate variability wave.

9. The portable electronic device of claim 1, wherein the pulse sensor is further configured as an operating button of the portable electronic device.

10. The portable electronic device of claim 1, wherein the respiration indicator is further configured to display information representative of a heart rate variability range for the subject.

11. A method for improving the physiological coherence of a subject using a portable electronic device, the method comprising the acts of:
 receiving pulse data from a subject;
 determining a power spectrum distribution of the pulse data,
 determining a heart rate variability waveform based on the pulse data having a power spectrum distribution (PSD);
 determining a coherence level for the subject derived from a PSD peak of said PSD;
 tracking the PSD peak of the PSD, wherein the PSD peak has an amplitude and frequency which vary over time;
 providing a coherence indication representative of the coherence level of the subject; and
 prompting the subject to breath at a desired respiration frequency which is associated with an increased coherence level.

12. The method of claim 11, wherein prompting comprises illuminating a plurality of light emitting diodes in a moving pattern of trailing lights.

13. The method of claim 11, wherein the coherence level is further based on a user-selectable coherence challenge level.

14. The method of claim 11, further comprising the act of adjusting the desired respiration frequency to account for the subject's natural respiration cycle.

15. The method of claim 11, further comprising the acts of determining the coherence level as a function of a relative amplitude of the PSD peak to a plurality of other peaks in the PSD.

16. The method of claim 15, wherein the coherence level increases as the PSD peak approaches the frequency range of between 0.03125 Hertz and 0.234 Hertz.

17. The method of claim 11, wherein the coherence level is characterized by at least one of a state of relaxation and increased positive emotions.

18. The method of claim 11, wherein the coherence level is characterized by a heart rate variability waveform having a sine-wave shape, and wherein the waveform is one of a respiratory sinus arrhythmia wave and a heart rate variability wave.

19. The method of claim 11, wherein receiving pulse data comprises receiving pulse data from a pulse sensor of the portable electronic device, and wherein the method further comprises receiving an operational command from the pulse sensor.

20. The method of claim 11, further comprising displaying information representative of a heart rate variability range for the subject.

21. A portable electronic device comprising:
a pulse sensor;
a coherence indicator;
a respiration indicator; and
a processor, electrically coupled to the pulse sensor, coherence indicator and respiration indicator, said processor configured to:
receive pulse data from the pulse sensor corresponding to a user,
determine a power spectrum distribution of the pulse data,
determine a heart rate variability waveform based on the pulse data having a power spectrum distribution (PSD),
determine a coherence level for the user derived from a PSD peak of said PSD,
track the PSD peak of the pulse data PSD, wherein the PSD peak has an amplitude and frequency which vary over time;
provide a coherence indication representative of the coherence level of the subject using the coherence indicator, and
prompt the subject, using the respiration indicator, to breath at a desired respiration frequency which is associated with an increased coherence level.

22. The portable electronic device of claim 21, wherein the respiration indicator comprises a plurality of light emitting diodes configured to illuminate in a moving pattern of trailing lights.

23. The portable electronic device of claim 21, wherein the coherence level is further based on a user-selectable coherence challenge level.

24. The portable electronic device of claim 21, wherein the processor is further configured to adjust the desired respiration frequency to account for the subject's natural respiration cycle.

25. The portable electronic device of claim 21, wherein the processor is configured to
determine the coherence level as a function of a relative amplitude of the PSD peak to a plurality of other peaks in the PSD.

26. The portable electronic device of claim 25, wherein the coherence level increases as the PSD peak approaches the frequency range of between 0.03125 Hertz and 0.234 Hertz.

27. The portable electronic device of claim 21, wherein the coherence level is characterized by at least one of a state of relaxation and increased positive emotions.

28. The portable electronic device of claim 21, wherein the coherence level is characterized by a heart rate variability waveform having a sine-wave shape, and wherein the waveform is one of a respiratory sinus arrhythmia wave and a heart rate variability wave.

29. The portable electronic device of claim 21, wherein the pulse sensor is further configured as an operating button of the portable electronic device.

30. The portable electronic device of claim 21, wherein the respiration indicator is further configured to display information relating to a heart rate variability range for the subject.

* * * * *